United States Patent

Plant Pat. 3,973

Patented Nov. 16, 1976

3,973

PEACH TREE

Claron O. Hesse, Kingsburg, Calif., assignor to The Regents of the University of California, Berkeley, Calif.

Filed Sept. 10, 1975, Ser. No. 612,163

Int. Cl.[2] A01H 5/03

U.S. Cl. Plt.—43 1 Claim

Figure 1:
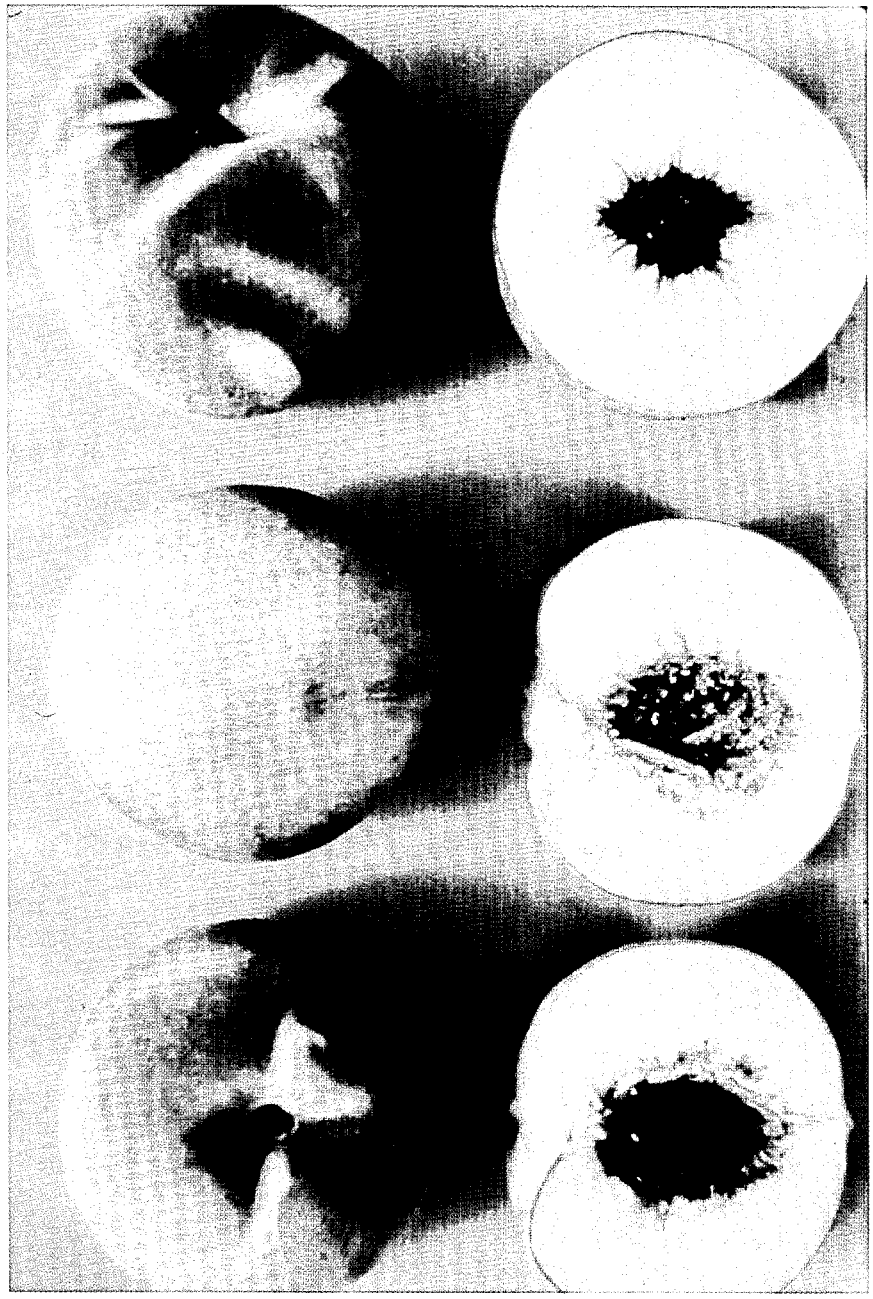

This invention relates to a new and distinct variety of peach tree which resulted from a complex cross, the pedigree of which is set forth below:

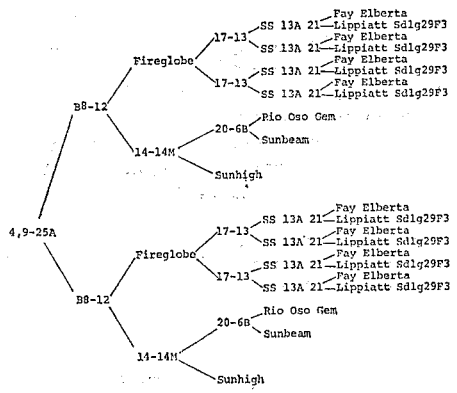

The last step self-pollination of B8-12 was made in 1960.

The invention of Selection 4,9-25A was discovered in 1965 and subsequently asexually multiplied at the Kearney Horticultural Field Station, Fresno County, Calif. in 1968. Thereafter the new variety was placed in several authorized grower-cooperative trial plots and tested. These tests indicated the merit of this new peach tree and resulted in its selection as a promising variety.

FIG. 1 of the accompanying drawing illustrates peaches of the new variety which are typical in size, shape and color, some of which are shown in half sections, pitted and unpitted, and in which some of the variations in the size and shape of the fruit, its pit, and the color of the skin and flesh of this variety are indicated.

A distinguishing characteristic of this new tree is its fruit which acquires a high red blush when mature enough for shipping and which becomes full red at maturity.

The fruit is further characterized by its solid flesh which is clear amber-yellow without red flecking until overripe on the tree, and its bright red cavity. The fruit of this new variety ripens a few days before Fay Elberta and after Suncrest and is of excellent eating quality, sweet, slightly subacid in flavor and of moderate aroma.

The varietal characteristics of this new peach tree described below in detail were observed upon its discovery and subsequently through its test period. The color terminology as used herein is in accordance with Ridgway, Color Standards and Color Nomenclature (1912 Edition).

Tree:

*Size.*—Medium, vigor medium; upright-spreading, with shape and density determined by pruning.

*Current seasons shoots.*—Light Cress Green, Plate XXXI, barely tinged red where exposed.

*Trunk.*—Medium stout; medium rough; brown (Chestnut Brown, Plate XIV).

*Branches.*—Brown to reddish brown (Chestnut Brown, Plate XIV to Hessian Brown, Plate XIII); bark rough; peeling off in recurved platelets which adhere tightly; on younger branches growth cracks longitudinally striated showing light brown beneath (Dresden Brown, Plate XV).

*Lenticels.*—Moderately numerous, medium size, relatively inconspicuous with low, raised lips.

*Flower buds.*—Plump, pubescent.

Leave: Midshoot leaves from shoots 18" to 22" long.

*Size.*—Medium large; 18.0±3.88 cm. long x 4.7 ±0.33 cm. wide, including petiole.

*Shape.*—Ovate-lanceolate to lanceolate; moderately recurved.

*Blade.*—Medium thick, dark green above (Dark Dull Yellow Green, Plate XXXII), slightly lighter beneath. Margin crenate, slightly wavy. Midrib Scheele's Green, Plate VI; lightly puberulent next to blade on the lower side. Blade usually slightly folded.

*Petiole.*—Short, 1.1±0.99 cm.; moderately stout; channeled on upper side.

*Glands.*—2–5, on apical portion of petiole and base of blade. Globose.

Flowers: 1–2 per node.

*Pedicel.*—Short, 2 mm. to 3 mm. medium, stout. Greenish (Scheele's Green, Plate VI).

*Corolla.*—Obconic; surface rugose, red (Ox-Blood Red, Plate I) to greenish, depending upon exposure. Glabrous. Nectaries, orange (Orange, Plate III), surface slightly irregular.

*Calyx lobes.*—Separate, ovate, pubescent dorsally and marginally, glabrous within. Reddish (Ox-Blood Red, Plate I) dorsally; green within with reddish veins. Cupped; margins entire. About 7 mm. long x 6 mm. wide at base. Lobes reflexed 90° or more at full anthesis.

*Petals.*—Nearly round to broad ovate about 18 mm. to 23 mm. long by 17 mm. to 22 mm. wide. Claw very short, stout. Margins nearly entire; only occasionally nicked or eroded; slightly wavy. Petals usually slight cupped. Color clear, light pink (Rose Pink, Plate XII) becoming rosaceous (Bordeaux, Plate XII) basally and at the claw with age. Showy phenotype.

*Stamens.*—About 50 in number. Filaments: Long to 15 mm., equal to style. White at anthesis. Becoming rosaceous with age. Anthers: Full, plump; bright red dorsally (Nopal Red, Plate I); yellow ventrally (Light Cadmium, Plate IV) and in creases. Pollen moderately plentiful, fertile.

*Pistil.*—Long, to 18 mm.; greenish; ovary small, ovate, heavily pubescent; style glabrous, except for basal few mm.; stigma capitate.

Fruit:

*Ripe.*—August 1 in 1973.

*Crop.*—Full for tree.

*Size.*—Medium or larger; length 74.43±4.40 mm. x cheek diameter 80.89±3.89 mm. x suture diameter 80.65±4.18 mm.; average weight of fruit 256.5±34.00 gms.

*Shape.*—Globose to slightly globose-truncate; quite regular; dorsal and ventral sides may be somewhat longer. Ventral aspect: broad elliptical regular; truncate at base. Axial Aspect: round, regular, smooth.

*Base.*—Flat, medium broad; sloping slightly toward ventral suture.

*Shoulders.*—Evenly rounded to the medium deep cavity. Usually slightly lower dorsally and often ventrally.

*Cavity.*—Medium depth, oval to round in outline, broadly acuminate conical.

*Suture.*—Nearly or a line mediumly; not at all or occasionally lightly creased in the cavity; rarely cleft at the shoulder; usually becoming a shallow groove apically. One side usually somewhat larger, especially apically resulting in a slightly raised lip of medium breadth and roundness.

*Apex.*—Rounded, usually sloping slightly ventrally; tip small in the depression or barely raised. Stylar scar a small, black dot or tip.

*Color.*—Ground color changing from greenish-yellow to yellow-amber with maturity (Bright Chalcedony Yellow, Plate XVII to Light Cadmium, Plate IV).

*Blush.*—Full or nearly so, washed red (Carmine, Plate I) over entire surface. Underlaid with somewhat darker blotches and streaks of darker red (Ox-Blood Red, Plate I); very attractive. Color develops to essentially full amount before maturation.

*Pubescence.*—Short, light.

*Flesh color.*—Medium yellow becoming deeper amber yellow (Light Orange-Yellow to Deep Chrome, Plate III); with increasing maturity; occasionally with a few specks of red, especially near or on ventral suture.

*Cavity color.*—Medium bright red (Carmine Red, Plate I) radiating into the flesh for a short distance only. With some whitish callous on the cavity surface.

*Adhesion.*—Full free to completely air free.

*Flesh.*—Texture; firm when full ripe; firm melting, moderately fine texture.

*Flavor.*—Sweet, slightly subacid; moderate aroma. Eating quality is excellent.

*Stone.*—Small to medium for fruit size; length 34.69 ±1.55 mm. x 19.38±1.29 mm. thick x 25.31 ±wide. Elliptical to ovate; moderately plump. Ventral edge more or less rounded; suture and wings sharp, not protruding; rather narrow; with deep incisions at each edge of the suture. Dorsal edge slightly raised usually narrowly and rather deeply grooved from base to apex. Apex a sharp tip of medium length, nearly or quite symmetrical. Surface pitted mediumly to sharply and incisively grooved apically, especially ventrally. Pits and grooves deep. Base very slightly and broadly necked; stem scar moderately large, oval. Color dark brown (Mahogany Red, Plate II), but bright medium red (Carmine Red, Plate I) at the base and basally along the ventral suture. Base slopes somewhat toward ventral suture.

*Seed.*—Medium size for species; oval, medium thickness; testas cream to light brown (Sanford's Brown Plate II) at maturity.

I claim:

1. The new and distinct variety of peach tree herein described and illustrated, and identified by the characteristics enumerated above.

No references cited.

ROBERT E. BAGWILL, Primary Examiner